United States Patent

Burbank et al.

[11] Patent Number: 5,931,829
[45] Date of Patent: Aug. 3, 1999

[54] METHODS AND SYSTEMS FOR ESTABLISHING VASCULAR ACCESS

[75] Inventors: Jeffrey H. Burbank, Boxford; James M. Brugger, Newburyport; Charles D. Finch, Clinton, all of Mass.; Gerald Beathard, Austin, Tex.; George W. Buffaloe, Arvada, Colo.

[73] Assignee: Vasca, Inc., Tewksbury, Mass.

[21] Appl. No.: 08/856,641

[22] Filed: May 15, 1997

Related U.S. Application Data

[60] Provisional application No. 60/036,124, Jan. 21, 1997.

[51] Int. Cl.⁶ .................................................. A61M 31/00
[52] U.S. Cl. .......................... 604/502; 604/4; 604/93; 604/264; 604/280
[58] Field of Search ........................ 604/93, 264, 280, 604/4, 49–53

[56] References Cited

U.S. PATENT DOCUMENTS

| | | | |
|---|---|---|---|
| 4,181,132 | 1/1980 | Parks | 128/399 |
| 4,892,518 | 1/1990 | Cupp et al. | 604/93 |
| 5,041,098 | 8/1991 | Loiterman et al. | 604/175 |
| 5,203,771 | 4/1993 | Melker et al. | 604/53 |
| 5,215,530 | 6/1993 | Hogan | 604/174 |
| 5,234,406 | 8/1993 | Drasner et al. | 604/51 |
| 5,281,199 | 1/1994 | Ensminger et al. | 604/93 |
| 5,417,656 | 5/1995 | Ensminger et al. | 604/93 |
| 5,562,617 | 10/1996 | Finch, Jr. et al. | 604/93 |

*Primary Examiner*—Wynn Wood Coggins
*Assistant Examiner*—Deborah Blyveis
*Attorney, Agent, or Firm*—Townsend & Townsend & Crew LLP

[57] ABSTRACT

A body lumen access system comprises a distal access cannula and a proximal access cannula. The distal access cannula is attached to or within the body lumen and the proximal access cannula is attached to an implantable port or is transcutaneously positioned and attached to a luer or other external connector. The distal and proximal access cannulas are usually implanted separately, cut to length, and attached at a subcutaneous junction location. Preferably, the proximal access cannula has a larger lumen diameter than that of the distal access cannula in order to reduce flow resistance within the cannula system. In some cases the distal and proximal access cannulas may be formed integrally.

131 Claims, 12 Drawing Sheets

METHODS AND SYSTEMS FOR ESTABLISHING VASCULAR ACCESS

The present application is a continuation-in-part of Provisional Application Ser. No. 60/036,124, filed on Jan. 21, 1997, the full disclosure of which is incorporated herein by reference.

BACKGROUND OF THE INVENTION

1. Field of the Invention

The present invention relates generally to the design and use of medical devices, and more particularly to a method and system for establishing temporary access to a patient's vascular system for hemodialysis and other extracorporeal blood treatments.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications which are limited in time, such as intravenous feeding, intravenous drug delivery, and the like, they are not suitable for hemodialysis and other extracorporeal procedures that must be repeated periodically, often for the lifetime of the patient.

For hemodialysis and other extracorporeal treatment regimens, a variety of transcutaneous catheters and implantable ports have been proposed over the years. Transcutaneous catheters, such as the Tesio catheter available from Med Comp and the Perm-Cath™ available from Quinton, comprise a single catheter tube having a distal end placed in a vein in an in-dwelling manner and a proximal end which extends through the skin and is which available for connection to a hemodialysis or other blood treatment system. Such catheter includes a DACRON® cuff disposed just beneath the skin in order to reduce the risk of infection.

Implantable ports, in contrast, are entirely subcutaneous and connected to a vein or an artery by a subcutaneous cannula. Access to the port is achieved by percutaneous placement of a needle or other connecting tube. Such ports typically comprise a needle-penetrable septum to permit percutaneous penetration of the needle. Recently, several valved-port designs have been proposed, where introduction of a needle or other access tube opens the valve to provide flow to the cannula which connects to the blood vessel.

Both the transcutaneous and implanted port vascular access systems suffer from certain disadvantages and limitations. For example, both such access systems permit only limited blood flow rates. In the case of transcutaneous catheters, the limited flow rates result from the generally small lumen diameters available in in-dwelling venous catheters. In the case of implanted port access systems, the limited flow rates have resulted from both the port structures and the relatively small lumen diameters available in the cannulas which connect the port to the blood vessel. Such limited blood flow rates are problematic since they prolong the duration of the associated extracorporeal blood treatment protocol, such as hemodialysis, hemofiltration, and apheresis.

The initial implantation of both the transcutaneous and implanted port vascular access systems has also been problematic. Such systems generally comprise a single catheter or cannula which is connected to or implanted within the blood vessel and brought to the external attachment point, i.e. either the implanted port or transcutaneous tract through the skin. The subcutaneous placement of the catheter or cannula is difficult in a number of respects. For example, catheters and cannulas having their distal ends implanted in the jugular vein are typically bent by an angle from 90° to 180° to locate their associated ports or catheter exit points at an appropriate location on the patient's chest. Such bends also can accommodate excess length in the connecting catheters and cannulas. The bends, however, are also subject to kinking and other problems. Thus, it would be desirable to provide methods and systems for implanting vascular access catheters and cannulas which can accommodate different patient characteristics and placement patterns.

An even more significant problem with prior transcutaneous and implanted port vascular access systems has been replacement. It is often necessary to replace a transcutaneous catheter when its distal end becomes dysfunctional due to plugging or other causes. Heretofore, it has usually been necessary to remove the entire catheter, including the subcutaneous cuff which has become ingrown in the tissue. In the case of implanted port systems, either the port or the cannula attached to the blood vessel could become dysfunctional. Heretofore, it has generally been necessary to remove both the port and the implanted cannula when either needs to be replaced. It would therefore be desirable to provide improved methods and systems which permit only a portion of the implanted system to be replaced when other portions of the system remain functional.

For these reasons it would be desirable to provide improved transcutaneous and implanted port access systems and methods for their implantation and replacement which would overcome at least some of the problems described above. In particular, it would be desirable if the vascular access systems could provide enhanced flow rates, preferably above at least 200 ml/minute, more preferably above 500 ml/minute, still more preferably above 600 ml/minute, and even more preferably above 700 ml/minute. Systems and methods of the present invention should also facilitate both initial implantation and, if necessary, subsequent replacement of system components with minimum trauma to the patient. At least some of these objectives will be met by the different aspects of the present application described below.

2. Description of the Background Art

U.S. Pat. Nos. 5,562,617 and 5,041,098 are exemplary of implantable systems employing cannulas extending between a port and a blood vessel for providing extracorporeal circulation. U.S. Pat. Nos. 5,417,656 and 5,281,199 show implantable ports which are connected to vascular cannulas via a transition region (FIG. 1A) and to a multiple branch cannula (FIG. 21). U.S. Patent No. 4,892,518 shows an implanted port with a transition region extending to a cannula. U.S. Pat. Nos. 5,234,406 and 5,215,530 show two-piece catheters having a distal portion which can be placed percutaneously. The '406 patent discloses a large diameter proximal portion to enhance the flow rate of anesthetics to the subarachnoid region of the spine. U.S. Pat. Nos. 5,203,771 and 4,181,132 show implantable connectors which provide for percutaneous access to implanted shunts.

Related co-pending applications, assigned to the assignee of the present application, include Ser. Nos. 08/745,903; 08/724,948; 08/634,634; 08/539,105; and 60/036,124.

The full disclosures of each of the U.S. Patents and co-pending applications listed above are hereby incorporated herein by reference.

SUMMARY OF THE INVENTION

The present invention provides improved methods and systems for accessing body lumens, particularly blood vessels, but also the peritoneal cavity, and the like. The systems comprise an access cannula, usually comprising a distal portion and a proximal portion, which is implanted from the body lumen to a proximal access site, typically an implanted port or a transcutaneous access location catheter. Distal access to the body lumen is effected by any one of a variety of access devices and techniques, such as in-dwelling cannulas, cross-tubes (T-catheters), end-to-side anastomosis, and the like. The methods and the systems of the present invention are particularly useful in that they both facilitate initial implantation of the access cannula system and simplify replacement of all or a portion of the access cannulas system should such replacement become necessary. The design of the access cannulas also minimize flow resistance, making the systems particularly compatible with high volume extracorporeal treatment protocols, e.g. those with flow rates above 200 ml/minute, usually above 500 ml/minute, and often above 600 ml/minute, and sometimes above 700 ml/minute or higher.

According to a first aspect of the method of the present invention, access to a body lumen in the patient is established by implanting a distal access cannula between the body lumen and a subcutaneous junction location. A proximal access cannula is implanted between the subcutaneous junction location and a catheter connection location located at a site remote to the body lumen. The length of at least one of the distal access cannula and the proximal access cannula is then adjusted (preferably both are adjusted, e.g. by cutting) so that the cannulas may be joined with an appropriate total length between the body lumen and the remote access site, i.e. neither too long nor too short. The proximal end of the distal access cannula is then connected to the distal end of the proximal access cannula, typically using a connector which is placed therebetween.

The location of the subcutaneous junction location can be virtually anywhere between the body lumen and the remote access site, and need not be on a straight path therebetween. Often, the access cannula will follow an arcuate or U-shaped path between the body lumen and the access site, and the subcutaneous junction location can be anywhere along such a path. In some cases, it may be desirable to dispose or create the subcutaneous junction location adjacent to the body lumen, e.g. within 0 cm to 5 cm, in order to reduce the number of incisions necessary to implant the total system. By locating the junction region adjacent to the body lumen, only a single incision and cavity need by made for connecting the distal access cannula to the body lumen and for connecting the proximal end of the distal access cannula to the distal end of the proximal access cannula, typically using the connectors described in more detail below. In other cases, however, it will be desirable to locate the subcutaneous junction away from the body lumen, usually from 5 cm to 50 cm from the body lumen. The subcutaneous junction location will usually not be adjacent to an implanted port.

The adjusting step preferably comprises adjusting the length of both the distal access cannula and the proximal access cannula. Adjusting typically comprises cutting the end of the cannula which will be located at the subcutaneous junction location. The cannula may be cut before it has been implanted (in which case it must be accurately sized prior to implantation), but will more usually be cut after it has been partially implanted and the end to be cut has been tentatively positioned at the subcutaneous junction location.

The distal access cannula implanting step comprises attaching the distal end of the distal access cannula to the body lumen in some manner. For example, the distal access cannula may be in the form of an in-dwelling venous catheter in which case its distal end is introduced through the blood vessel wall, typically by a distance of at least 1 cm, usually by 5 cm or more, either through an incision or through a needle-penetration. Alternatively, the distal end of the distal access cannula may be in the form of a cross-tube (T-catheter) which is implanted through an incision in the blood vessel wall, as described in co-pending application Ser. Nos. 08/539,105 and 08/724,948, the full disclosures of which are incorporated herein by reference. As a still further alternative, the distal end of the distal access cannula may be sutured to the blood vessel wall via an end-to-side anastomosis, as described in U.S. Pat. No. 5,562,617, the full disclosure of which is incorporated herein by reference.

The proximal access cannula implantation step may also comprise a number of approaches. For example, the proximal access cannula may be positioned transcutaneously so that its proximal end lies permanently outside the patient's body. The proximal end would then have a standard luer or other fitting for connection to an external catheter for extracorporeal circulation or other purposes. The proximal access cannula implanting step may alternatively comprise subcutaneously implanting a port which is connected to a proximal end of said cannula. The port will be adapted for receiving a percutaneous needle or other access tube to permit connection to an external catheter for extracorporeal circulation or other purposes. Numerous conventional subcutaneous ports have been described in the medical and patent literature, but the present invention is particularly suitable for use with the high-volume, needle-actuated port described in co-pending application Ser. No. 60/036,124, the full disclosure of which is incorporated herein by reference, from which the present application is a continuation-in-part.

The distal access cannula and the proximal access cannula may have substantially equal lumenal cross-sectional areas, typically having equal diameters in the range from 1 mm to 10 mm, usually from 3 mm to 10 mm, but will often have unequal cross-sectional areas. As described in more detail in connection with a second aspect of the method of the present invention, it will often be desirable to provide a larger cross-sectional area in at least a portion of the proximal access cannula, and optionally in a portion of the proximal end of the distal access cannula, in order to reduce the total flow resistance presented by the access cannula system.

The connecting step of the method for establishing body lumen access typically comprises providing an intermediate connector having a first attachment aperture for attaching a proximal end of the distal access cannula and a second attachment aperture for connecting a distal end of the proximal access cannula. While the respective ends of the distal and proximal access cannulas could be connected directly, e.g. one or both could have a connector mounted thereon, it is preferable to provide an intermediate connector which is capable of attaching a "bare" tube. In this way, the access cannulas may be cut to their desired lengths, and the resulting "bare" cut end attached to the intermediate connector in a convenient manner, typically by placing over an end of the connector and tying using suture or other filament.

The intermediate connectors may be linear, i.e. with a straight lumen so that the distal and proximal access cannulas are coaxially aligned at their point of attachment. Alternatively, the connectors can be non-linear, e.g. with their first and second attachment apertures disposed at a relative angle in the range from 45° to 270°, preferably from 90° to 180°0, in order to dispose the distal and proximal access cannulas in a non-linear fashion.

In a particularly preferred aspect of the present invention, the remote connectors may be adapted to connect a large diameter proximal access cannula to a smaller diameter distal access cannula. In some cases, the connector itself may provide for a transition in the lumen diameter connecting the two cannulas, but such a transition is not necessary, and the change of diameter may be provided within one of the cannulas, preferably the distal access cannula. Such connectors are particularly useful for providing the low flow resistance access cannulas described above.

According to a second aspect of the method of the present invention, access between a body lumen and an implanted port is provided by a subcutaneous access cannula having a lumen therethrough. Improved low flow resistance access is provided by implanting a cannula having an enlarged lumen in a region proximal to the body lumen penetration than at and/or distal to the body lumen penetration. Typically, for intravascular access, the cannula lumen will have an inner diameter at and/or distal to the body lumen wall penetration in the range from 1 mm to 6 mm. By providing a cannula lumen (inner) diameter proximal to the body lumen penetration in the range from 3 mm to 10 mm, significantly reduced flow resistance can be achieved.

In a third aspect of the method of the present invention, access to a body lumen in the patient is established by providing an access cannula having a small diameter distal region and a large diameter proximal region. The access catheter is implanted so that the small diameter distal region is connected to or within the body lumen and with the distal end of the large diameter proximal region located subcutaneously, usually but not necessarily at a subcutaneous junction region as described above. The proximal end of the access cannula is available for connection to an external catheter by any of the methods described above.

The small diameter distal region and/or the large diameter proximal region may have uniform or non-uniform diameters along their entire lengths. While the diameters of each region will typically be uniform, in some cases it may be desirable to provide diameters which increase in the proximal direction, where the increase can be tapered, stepped, or irregular. In the case of access catheters which comprise two (or more) pieces, the small diameter distal region will often correspond to the distal access cannula described above. Alternatively, the distal access cannula can itself include the small diameter distal region and expand to the large diameter proximal region, with the proximal access cannula also having a large diameter after the subcutaneous connection.

In a fourth aspect of the methods of the present invention, an implanted cannula system may be replaced by separately removing either a distal portion or a proximal portion thereof. The methods comprise surgically exposing a portion of the access cannula while leaving at least one of the distal end (attached to a body lumen) and the proximal portion unexposed. The access cannula is disconnected at the site where it has been exposed (typically by removing one end from a remote connector as described above) and thereafter replacing one of the distal portion and the proximal portion while leaving the other in place. The replaced section can then be connected to the previously implanted section in order to reestablish access. Typically, the entire distal end of the cannula will be exposed when it is desired to replace the distal portion. Alternatively, the entire proximal portion of the cannula may be exposed when it is desired to replace the proximal portion. Alternatively, when replacing the proximal portion which is connected at its proximal end to an implanted port, it may only be necessary to surgically expose the port and the distal end of the proximal portion leaving the intermediate portion thereof subcutaneously implanted.

The present invention further provides systems for establishing access to a body lumen in a patient. The systems comprise a distal access cannula having a distal end, a proximal end, and a lumen therethrough. The distal end of the distal access cannula is adapted for connection to the body lumen, by any of the techniques described above, to provide fluid communication between the body lumen and the distal cannula lumen. The system further comprises a proximal access cannula having a distal end, a proximal end, and a lumen therethrough. The proximal end of the proximal access cannula is adapted for connection to an external catheter to provide fluid communication between the catheter and the proximal cannula lumen. Such external connection can be via a transcutaneous catheter, an implanted port, or any other conventional means. The system still further comprises a subcutaneously implantable connector for directly connecting the proximal end of the distal catheter to the distal end of the proximal catheter. By "directly" it is meant that the connector provides for substantially unimpeded flow therethrough, e.g. an unobstructed flow lumen. One of the objectives of the system of the present invention is to reduce flow resistance in the access cannula so the inclusion of flow limiting or control devices within the connector is contraindicated.

The connector preferably comprises a body having a first attachment aperture, a second attachment aperture, and an unobstructed flow lumen therethrough. Optionally, the first attachment aperture can branch into a plurality of additional attachment apertures so that a single proximal access cannula can be connected to a plurality of distal access cannulas, or vice versa. The flow lumen(s) through the body may be coaxial or parallel, but can also be curved or deflected so that the first attachment aperture and second attachment aperture define an angle therebetween, typically in the range from 45° to 270°, preferably in the range from 90° to 180°. Optionally, the lumen through the connector body may be flared, tapered, or stepped in one direction or the other in order to provide a transition from a small diameter at one end to a larger diameter at the other end.

The present invention further comprises kits which comprise a system including a distal access cannula and a proximal access cannula, such as any of those described above, together with instructions for use according to the methods described above. The systems and instructions are incorporated into a sterile or non-sterile package, such as a pouch, box, tray, or the like. The instructions may be printed on a package insert (a separate sheet) and/or may be printed on a portion of the packaging. The kits of the present invention may further comprise any one of the system components packaged together with instructions for use of that component according to a method of the present invention, e.g. replacement of that component within a previously implanted system.

DESCRIPTION OF THE SPECIFIC EMBODIMENTS

Figure 1:
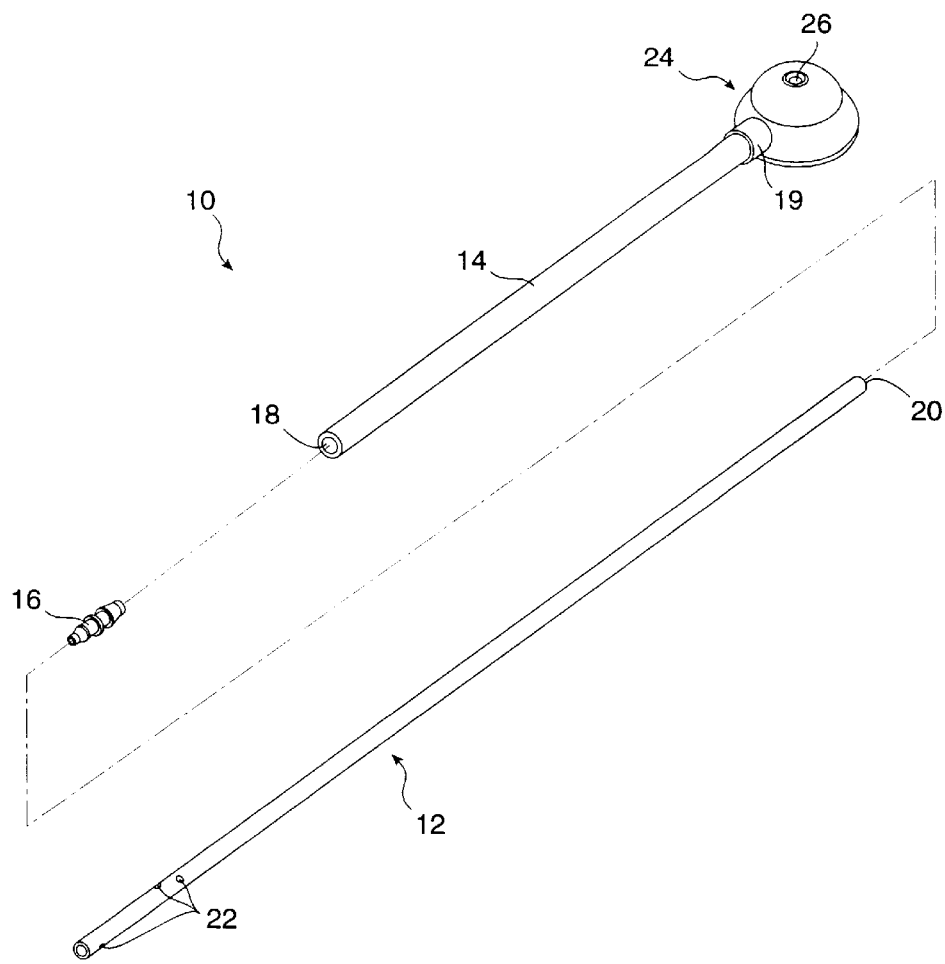
FIG. 1 is an isometric view of a first embodiment of a body lumen access system constructed in accordance with the principles of the present invention and comprising an indwelling venous cannula, an implantable port having a proximal access cannula attached thereto, and a connector for connecting the proximal access cannula to the in-dwelling venous cannula.

The present invention provides methods and apparatus for facilitating percutaneous and transcutaneous access to a body lumen of a patient. Exemplary body lumens, include blood vessels, the peritoneal cavity, and the like. The methods are particularly useful for accessing blood vessels, including both arterial blood vessels and venous blood vessels. While the remaining description is directed particularly at blood vessels, it will be appreciated that the invention applies to all body lumens and cavities where selective percutaneous access might be desired.

For percutaneous access, ports are implanted subcutaneously so that a passage therein lies a short distance beneath the surface of the patient's skin, typically being within 3 mm to 20 mm of the skin's surface. An access tube may then be percutaneously inserted into the passage in the access port in order to provide a connection to the blood vessel via the access port. For transcutaneous access, a catheter (usually defining a proximal access cannula according to the present invention) is implanted through the patient's skin with a proximal end of the catheter adapted for connection to an external catheter. In both cases, access can be provided for a variety of purposes, usually involving withdrawal of blood, the extracorporeal treatment of the withdrawn blood, and/or the return of the treated blood to the patient. Such extracorporeal blood treatment will most often be for hemodialysis, but can also be for hemofiltration, hemodiafiltration, apheresis, and the like. In addition to extracorporeal treatment, the access port of the present invention can be used for perfusing drugs, fluids, and other materials directly into a patient's circulation for a variety of purposes.

Apparatus according to the present invention will comprise access cannulas, usually but not necessarily including both a distal access cannula which is connected to or implanted within the body lumen and a separate proximal access cannula which is connected to an implanted port or transcutaneously positioned through the patient's skin. A proximal end of the distal access cannula is connected or connectable to a distal end of the proximal access cannula at a subcutaneous junction region, typically by a connector. The cannulas will typically comprise polymeric tubes extruded from conventional, biocompatible catheter materials, such as silicone rubber, polyurethane, and the like. The distal access cannula will typically have a low profile, particularly when all or a distal portion thereof is intended for implantation in a venous lumen. Exemplary distal catheters will have a length in the range from 5 cm to 45 cm, usually from 10 cm to 30 cm, an outer diameter in the range from 2 mm to 8 mm, usually from 3 mm to 6 mm, and a lumen diameter in the range from 1 mm to 6 mm, usually from 2 mm to 5 mm. The proximal access cannula will have a length in the range from 3 cm to 45 cm, usually from 5 cm to 15 cm, an outer diameter in the range from 4 mm to 11 mm, usually from 6 mm to 8 mm, and a lumen diameter in the range from 3 mm to 10 mm, usually from 5 mm to 7 mm. The access cannulas will usually be tubes having uniform diameters along their entire lengths, but may have tapered, stepped, or other variations in diameter, as described previously. The distal end of the proximal access cannula and proximal end of the distal access cannula will usually be uniform over a length sufficient to permit cutting, where the cut end of the cannula will have identical diameter and other properties so that the cut end may fit over an attachment aperture on the remote connector, as described in more detail below.

As described above, the access cannula comprises at least a discrete distal portion and a discrete proximal portion, where the portions are separate and connectable through a connector. In another aspect of the apparatus of the present invention, the distal and proximal portions of the access cannula may be formed integrally with the distal portion having a reduced diameter and the proximal portion having an enlarged diameter to reduce the overall flow resistance presented by the access cannula. The lengths of such catheters can be adjusted by cutting at either the proximal end or the distal end, but the transition region where the diameter changes will generally be integrally formed and unavailable for cutting.

Referring now to FIG. 1, an access system 10 according to the present invention comprises a distal access cannula 12, a proximal access cannula 14, and a connector 16 adapted for connecting a distal end 18 of the proximal access cannula to a proximal end 20 of the distal access cannula. The distal access cannula 12 is in the form of an in-dwelling venous catheter and includes a plurality of apertures 22 near its distal end to increase blood inflow or outflow through the cannula. The outer diameter of the venous access cannula 12 (as least over a distal portion thereof and usually over its entire length) will typically be in the range from 2 mm to 8 mm, preferably from 3 mm to 6 mm, and the lumenal diameter will be in the range from 1 mm to 6 mm, preferably from 2 mm to 5 mm.

An implantable port 24 is secured to a proximal end 19 of the proximal access cannula 14. The port 24 can be integrally or removably secured to the end 19, both of which are described in co-pending application Ser. No. 60/036,124, the full disclosure of which has been previously incorporated herein by reference. The port 24 provides for percutaneous access to the access system 10 by means of a needle or other access tube which is introduced through the patient's skin into an orifice 26 at the top of the port. Implantation of the access system 10 will be described in more detail in connection with FIGS. 11A and 11B below.

Figure 16:
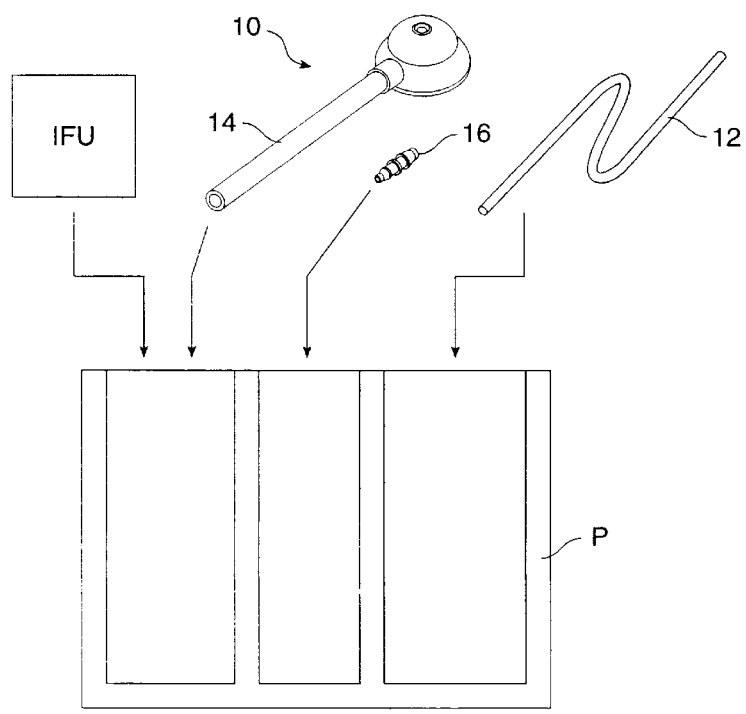
FIG. 16 illustrates a kit according to the present invention comprising a body lumen access system together with instructions for use (IFU) and a package.

The system 10 of FIG. 1, or any of the other systems and individual components thereof, may be packaged together with instructions for use (IFU), as shown in FIG. 16. A conventional package, which may be a pouch P or any other suitable package, such as a tray, box, tube, or the like, contains the system 10 with the different components being optionally held in different, isolated pockets 200, 202, and 204 in the pouch P. Usually, the system 10 will be sterilized within the package, e.g. by radiation or ethylene oxide, and the instructions are provided on either the package itself or a separate printed sheet. The instructions will set forth any of the aspects of the method of the present invention described herein.

Figure 1A:
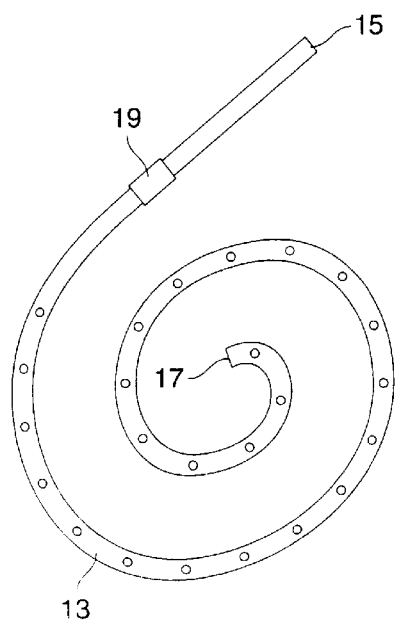

Referring now to FIG. 1A, the system 10 may be modified for use in peritoneal dialysis by substituting a pigtail catheter 13 for the distal access cannula 12. The pigtail catheter has a proximal end 15 adapted to be connected to the connector 16 and a distal end 17 which is similar in design to a conventional peritoneal dialysis catheter. The catheter 13 includes a cuff 19 which is implanted in the peritoneal wall, and the proximal end can be trimmed to join the connector 16 in the same manner as described below for vascular access.

Figure 2:
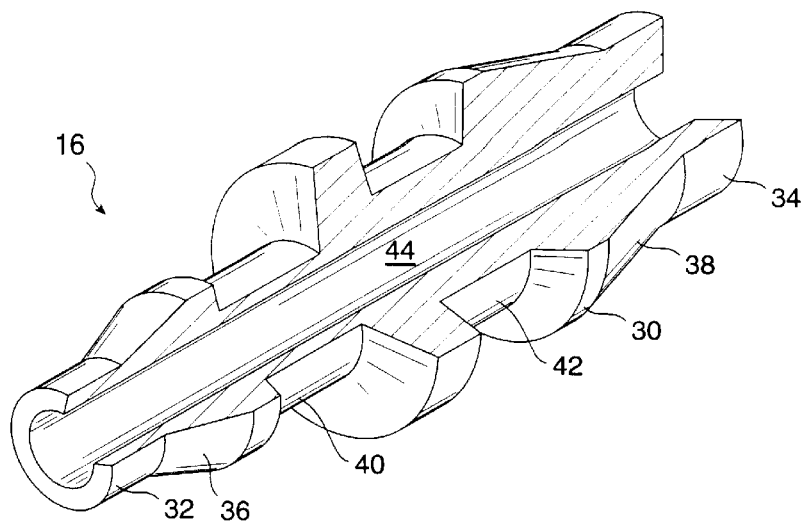
FIG. 2 is a detailed view of the connector of FIG. 1, shown in section.

Referring now to FIG. 2, the connector 16 comprises a body 30, typically composed of a biocompatible metal or thermoplastic, such as titanium. The connector body 30 defines a first attachment aperture 32, typically having a relatively small diameter to receive the proximal end 20 of the distal access cannula 12 (where the end 20 may be cut or trimmed prior to connection), and a large diameter connection aperture 34 adapted to receive the distal end 18 of the proximal access cannula 14 (which also may be cut or trimmed prior to connection). Each attachment aperture 32 and 34 has a conical portion 36 and 38, respectively, and a reduced diameter region 40 and 42, respectively, to facilitate attachment of the tubular ends of the access cannulas. In particular, the tubular ends, which are typically silicone rubber or other elastomeric material, are pushed over the conical region and into the reduced diameter region. Thereafter, the ends of the cannulas can be tied to the reduced diameter region using suture or other biocompatible material. A lumen 44 through the connector body 30 can have a uniform diameter along its entire length, usually from 1 mm to 10 mm, or can be tapered to increase in diameter toward the larger attachment aperture 34 intended to connect to the proximal access cannula 14.

Figure 3:
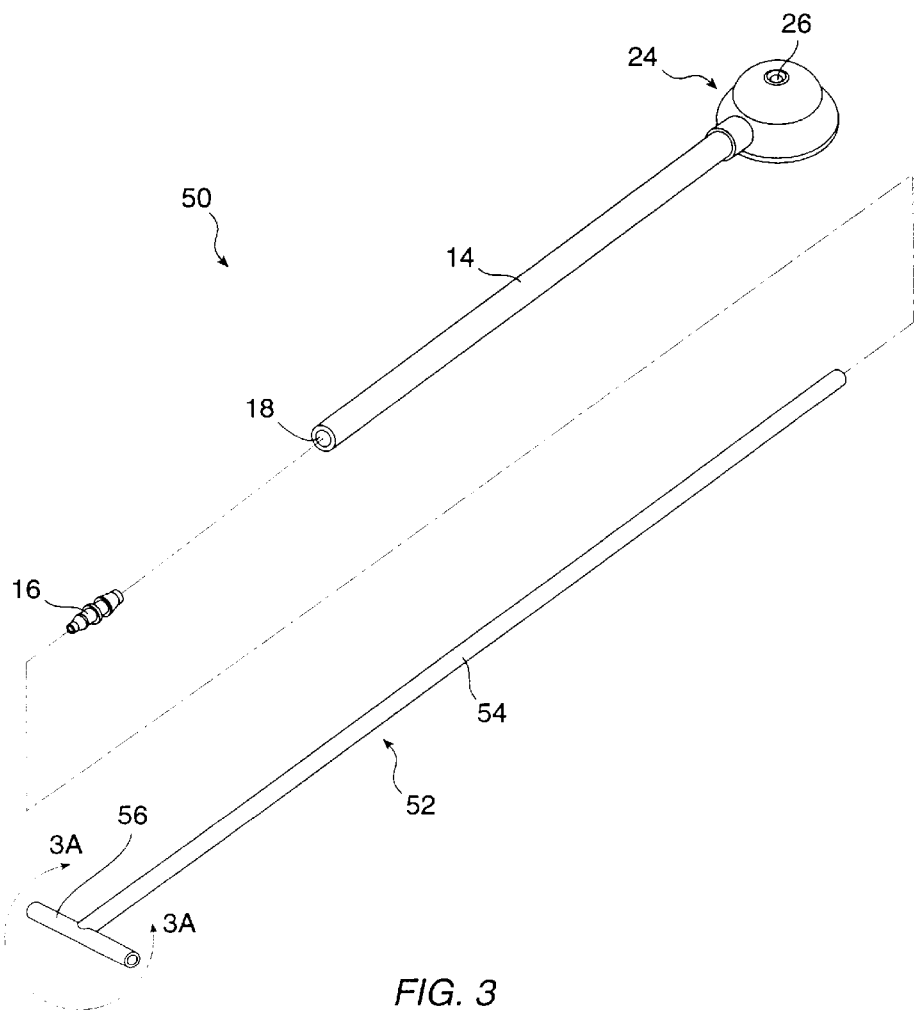
FIG. 3 is an isometric view of a second embodiment of a body lumen access system constructed in accordance with the principles of the present invention and comprising a distal access cannula having a cross-tube at its distal end, an implantable port having a proximal access cannula attached thereto, and a connector for connecting the distal access cannula to the proximal access cannula.
Figure 3A:
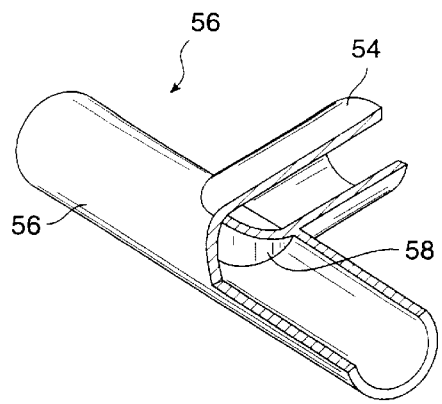
FIG. 3A is a detailed view of the distal end of the distal access cannula of FIG. 3.

Referring now to FIG. 3, a second access system 50 constructed in accordance with the principles of the present invention comprises a proximal access cannula 14 and connector 16, generally as described above in connection with the embodiment of FIG. 1. A distal access cannula 52 generally comprises an axial tubular body 54 having the dimensions generally set forth above, but terminating at its distal end in a cross-tube 56 as best illustrated in FIG. 3A. The cross-tube is in the form of a T-catheter, described in detail in co-pending applications Ser. Nos. 08/539,105 and 08/724,948, the full disclosures of which are incorporated herein by reference. The cross-tube 56 is intended for implantation within the lumen of a blood vessel in a minimally intrusive manner. A valve 58, typically a slit valve, is provided at the distal end of the tube 54 to inhibit blood flow into the lumen of tube 54 in the absence of a differential pressure. Thus, blood flow into the tube will be prevented unless there is a positive or negative pressure applied through the port 24 in order to effect the inflow or outflow of blood.

Figure 4:
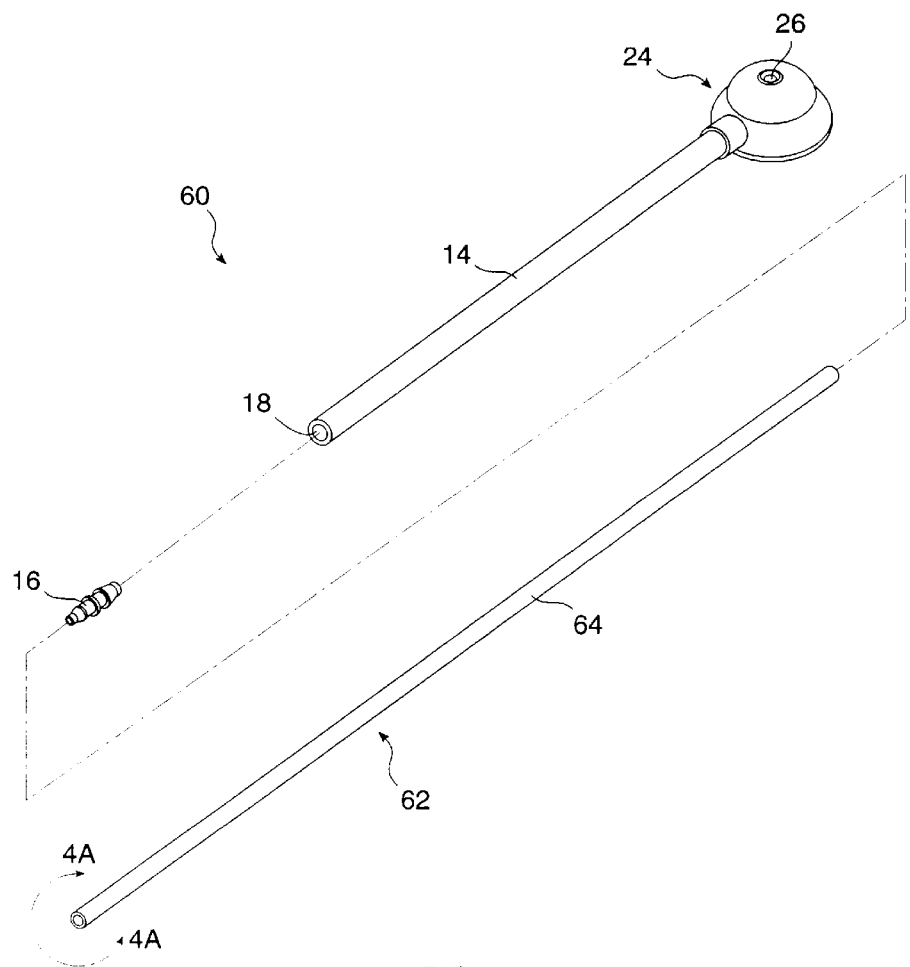
FIG. 4 is an isometric view of a third embodiment of a body lumen access system constructed in accordance with the principles of the present invention and comprising a distal access cannula having a distal end adapted for connection to a body lumen by an anastomosis, an implantable port having a proximal access cannula attached thereto, and a connector for connecting the distal access cannula to the proximal access cannula.
Figure 4A:
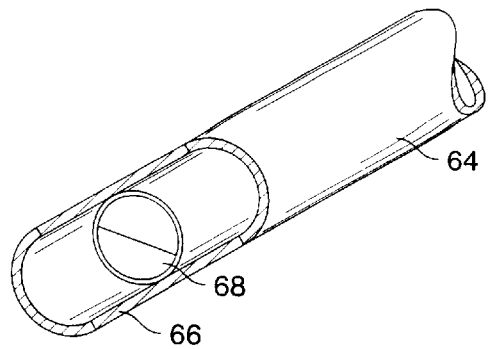
FIG. 4A is a detailed view of the distal end of the distal access cannula of FIG. 4.

A third access system 60 constructed in accordance with the principles of the present invention is illustrated in FIG. 4. Access system 60 comprises a proximal access cannula 14 and connector 16, generally as described above in connection with FIG. 1. Distal access cannula 62 comprises a tubular member 64 terminating at its distal end in a suturing cuff 66, generally as illustrated in FIG. 4A. A membrane 68 having a slit valve therein is provided to prevent flow into or out of the lumen of tube 64 in the absence of a differential pressure. Suturing of the distal access cannula 64 to a blood vessel or other body lumen is described in U.S. Pat. No. 5,562,617, the full disclosure of which has previously been incorporated herein by reference.

Figure 5:
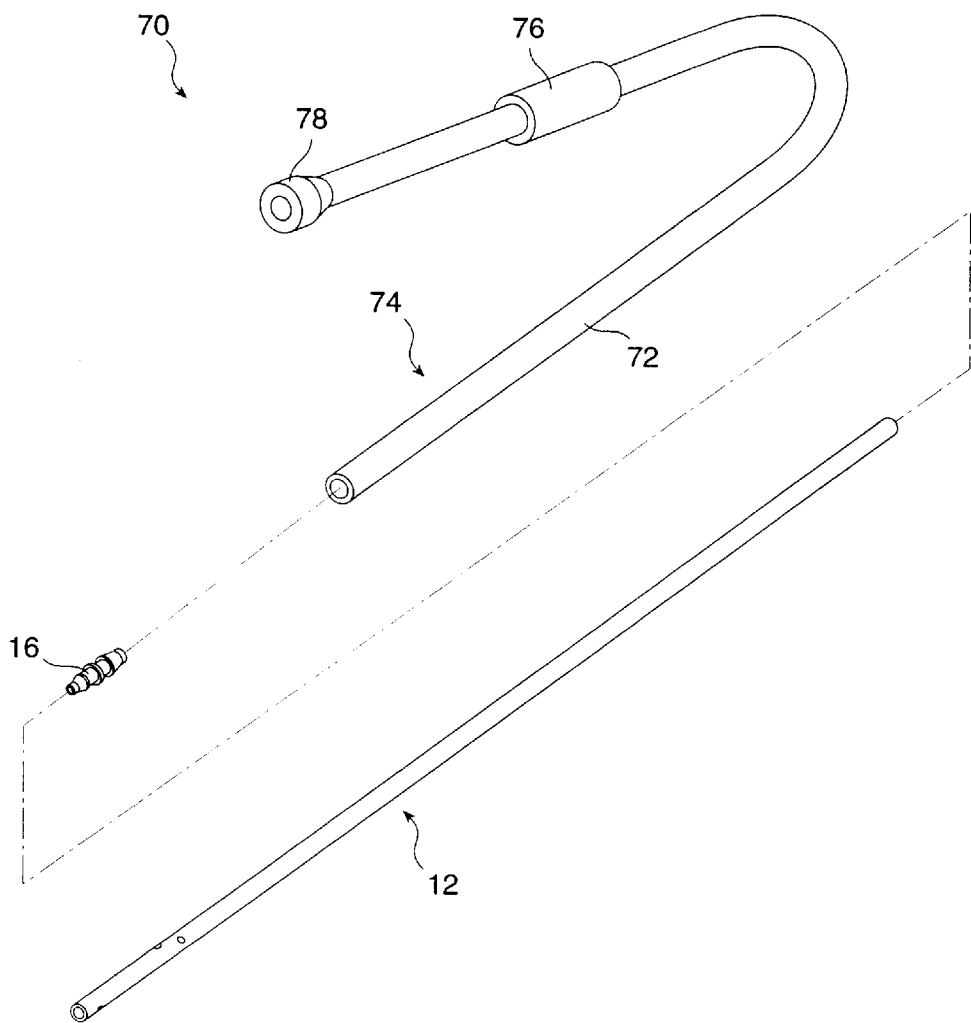
FIG. 5 is an isometric view of a fourth embodiment of a body lumen access system constructed in accordance with the principles of the present invention and comprising an in-dwelling venous cannula, a transcutaneous proximal access cannula, and a connector for connecting the in-dwelling venous cannula to the transcutaneous proximal access cannula.

A fourth access system 70 constructed in accordance with the principles of the present invention is illustrated in FIG. 5. The access system 70 comprises a distal access cannula 12 and connector 16, generally as described above in connection with FIG. 1. A proximal access cannula 72 is intended for transcutaneous placement through a patient's skin, as described in more detail in connection with FIG. 12 below. The proximal access cannula will comprise a distal end 74 which may be trimmed for connection to the connector 16. The proximal access cannula 72 will preferably comprise a cuff 76 which is intended to be implanted immediately beneath the patient's skin and to inhibit bacterial contamination through the cannula, as is generally known for venous in-dwelling catheters. A standard luer or other connector 78 will be provided at the proximal end of the access cannula 72 to permit connection to an external catheter.

Figure 6:
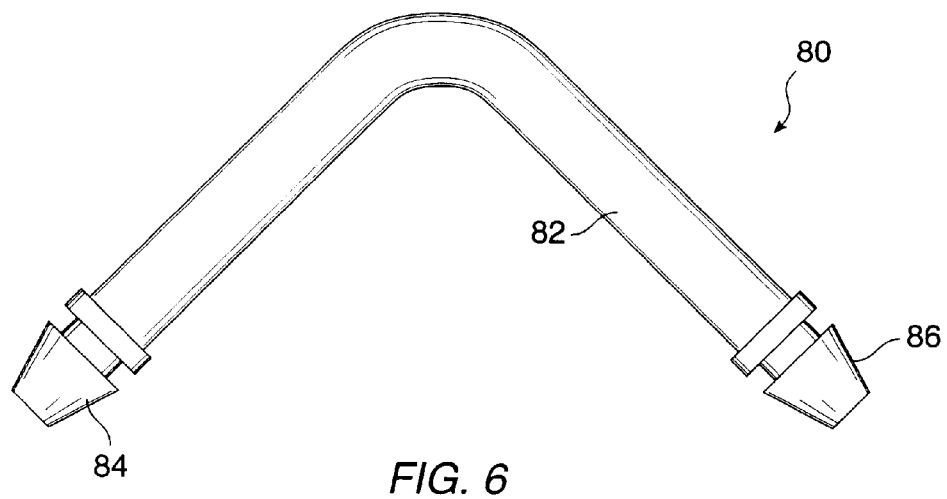
FIG. 6 illustrates a connector having a 90° bend.
Figure 7:
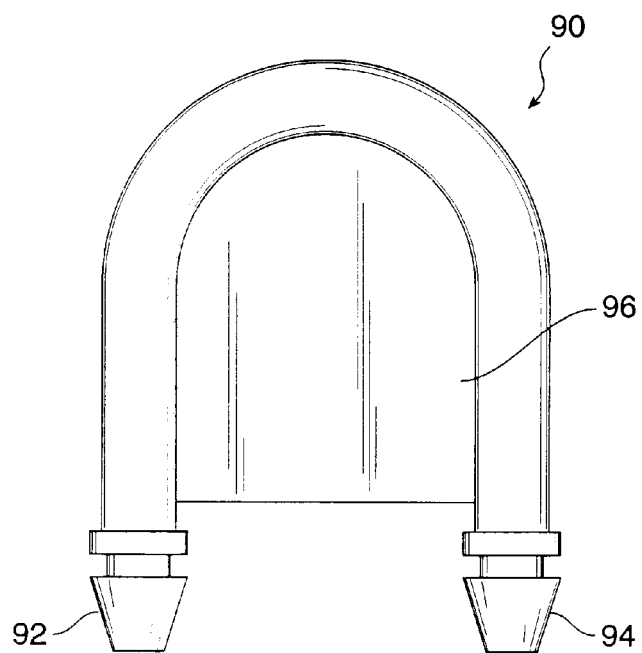
FIG. 7 illustrates a connector having a 180° bend.

The connector 16 provides a linear attachment of the distal access cannula to the proximal access cannula. In many cases, it will be desirable to provide a non-linear connection to facilitate positioning of the remote access site relative to the body lumen access site. A connector 80 which provides for a 90° relative angle between the distal and proximal access cannulas is illustrated in FIG. 6. The connector 80 comprises a bent tube 82 having a first attachment aperture 84 and a second attachment 86. As illustrated, the attachment apertures are identical, but they could easily have different sizes intended for attaching to a larger proximal access cannula and a smaller distal access cannula. A second bent connector 90 is illustrated in FIG. 7. Connector 90 is U-shaped and provides for a 180° turn between attachment aperture 92 and attachment aperture 94. Again, the attachment apertures 92 and 94 are illustrated as having the same size, but will frequently different sizes intended to attach different sized cannulas. The connector 90 also includes a web 96 spanning the region between adjacent legs of the connector. The web 96 is intended to prevent tissue in-growth around the connector, thus facilitating removal should that become necessary. The web 96 also provides a relatively large target for a surgeon attempting to access the connector for replacement of either cannula, with or without replacement of the connector. Without such a connector, there is significant risk that the surgeon attempting to access the subcutaneous junction region where the connector is positioned will accidentally cut or otherwise damage one of the cannulas which are composed of a silicone material which can easily be cut.

Figure 8:
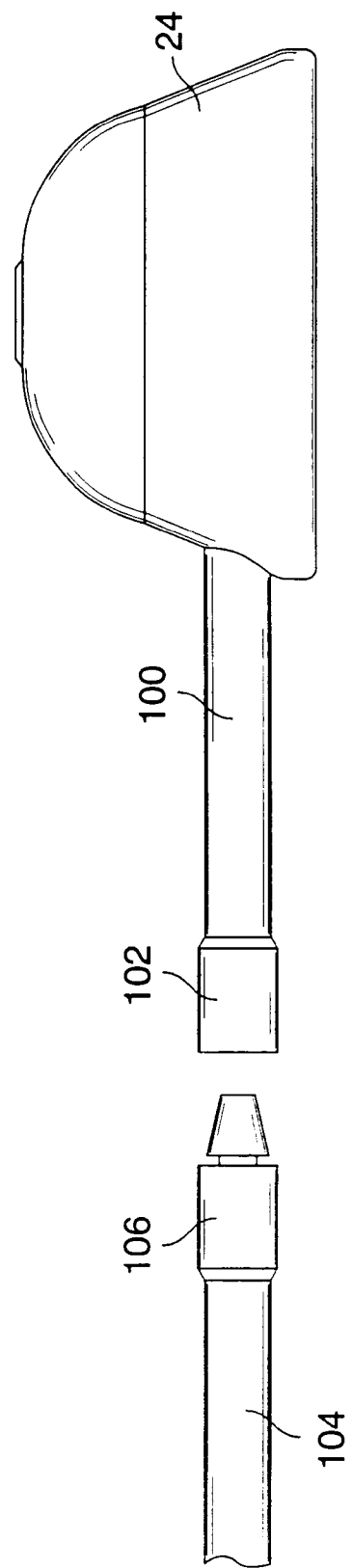
FIG. 8 illustrates an implantable port having an integral proximal cannula and a distal access cannula, wherein both the proximal cannula and the distal cannula have integral connectors thereon.

A less preferred access system according to the present invention is illustrated in FIG. 8. This system is described in co-pending parent Application Ser. No. 60/,036,124, the full disclosure of which has previously been incorporated herein by reference. Implantable port 24 comprises an integral proximal access cannula 100 having an integral connector 102 at its distal end. A distal access cannula 104, which may be in any of the forms described above, comprises an integral connector 106 at its proximal end, where the connectors 102 and 106 are intended for mating. While the assembly illustrate in FIG. 8 provides many of the advantages described herein above, such as the ability to provide for a larger lumen diameter in the proximal access cannula 100 and the ability to separately remove and replace either the proximal access cannula (together with the port 24) or the distal access cannula 104, it lacks many of the other advantages described above. In particular, by providing permanently affixed connectors 102 and 106, it is not possible to trim the ends of the cannulas which need to be connected. Also, the integral connection of the proximal access cannula 100 to the port 24 would prevent separate replacement of those two components.

Figure 9:
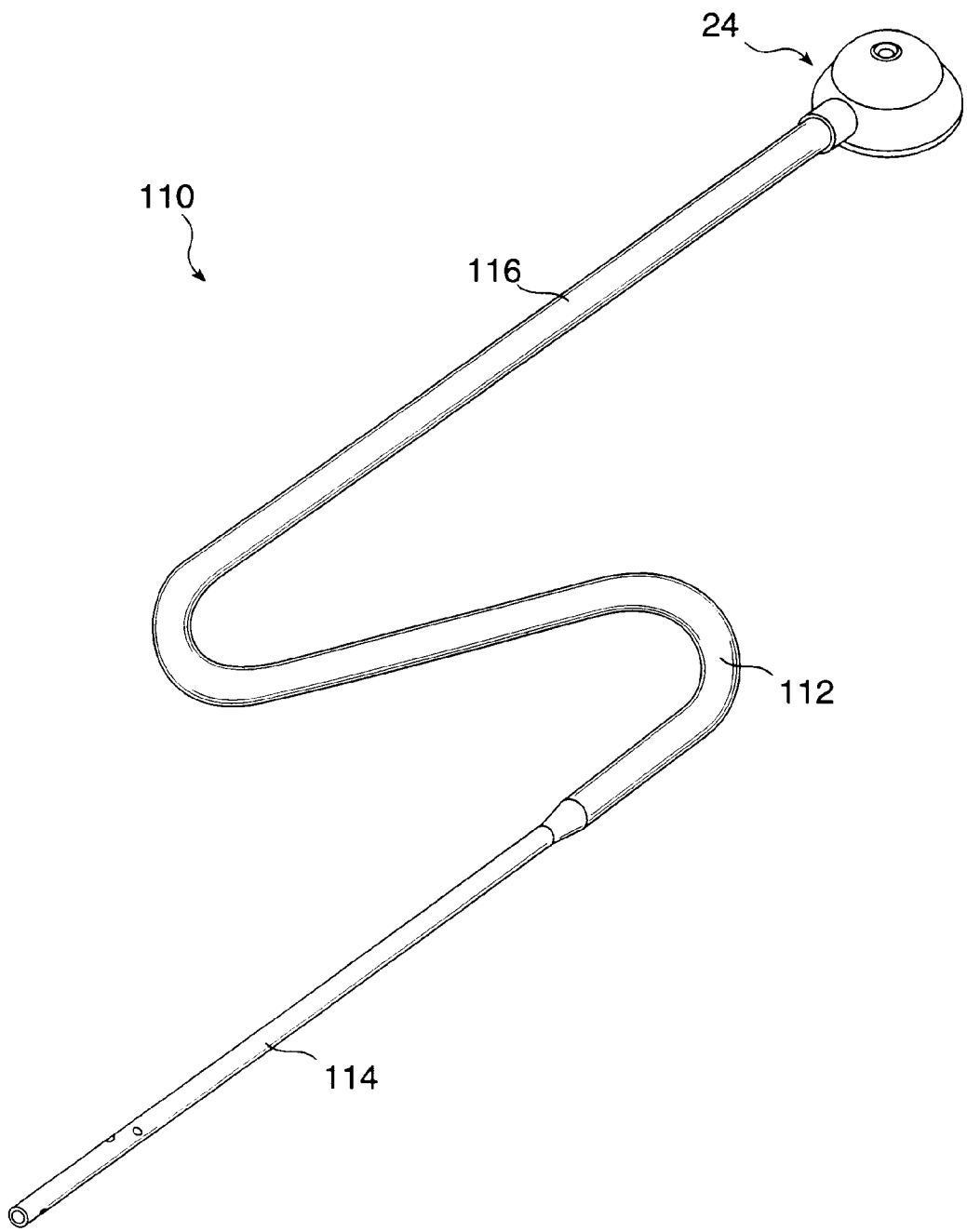
FIG. 9 illustrates a single-piece access cannula having a small diameter distal end and a large diameter proximal end, wherein the proximal end of the proximal portion of the cannula is attached or attachable to an implantable port.

Referring now to FIG. 9, a sixth access system 110 constructed in accordance with the principles of the present invention comprises a single-piece access cannula 112 having a small diameter distal portion 114 and a large diameter proximal portion 116. The proximal end of the proximal portion 116 is connected to an implantable port 24, generally as described above, but could also be fashioned as a transcutaneous catheter. The distal portion 114 of the access cannula 112 is shown as an in-dwelling catheter, but could be fashioned as any of the other distal cannulae described above, including the cross-tube configuration and the suturing cuff configuration. The access system 110 will have the advantages of the present invention with regard to reduced flow resistance, but is less preferred since it will not have the ability for improved implantation and improved replacement as described in more detail below.

Figure 10:
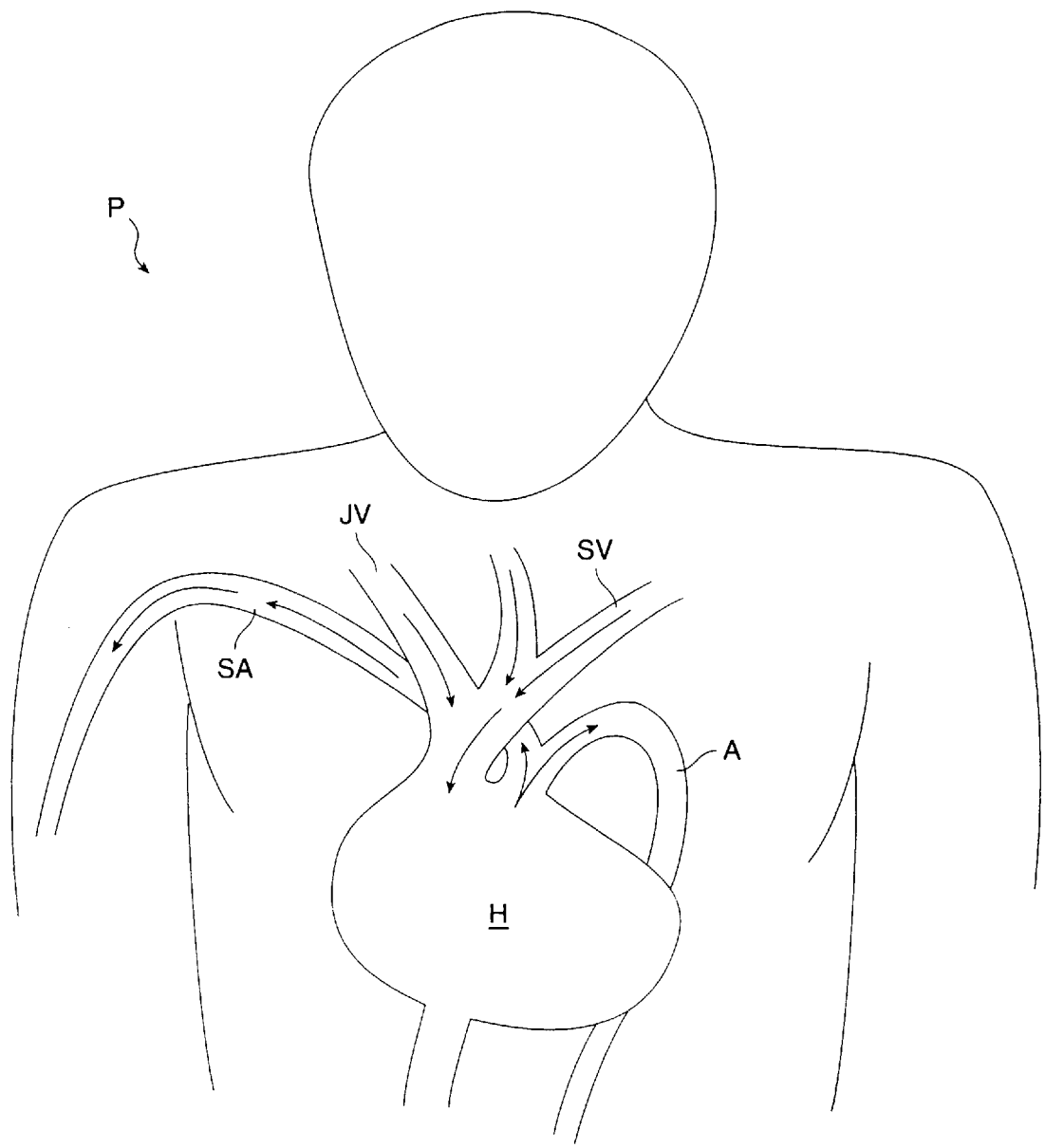
FIG. 10 illustrates patient vasculature to which the implantable access systems of the present invention can be connected.

The body lumen access systems described above are particularly suitable for establishing percutaneous and transcutaneous access to single or multiple locations in the patient's vasculature, including both the arterial and venous vasculature. As illustrated in FIG. 10, the arterial and venous vasculature of patient P in the region immediately surrounding the heart H includes the jugular vein JV, the subclavian vein SV, the subclavian artery SA, and the aorta A.

Figure 11A:
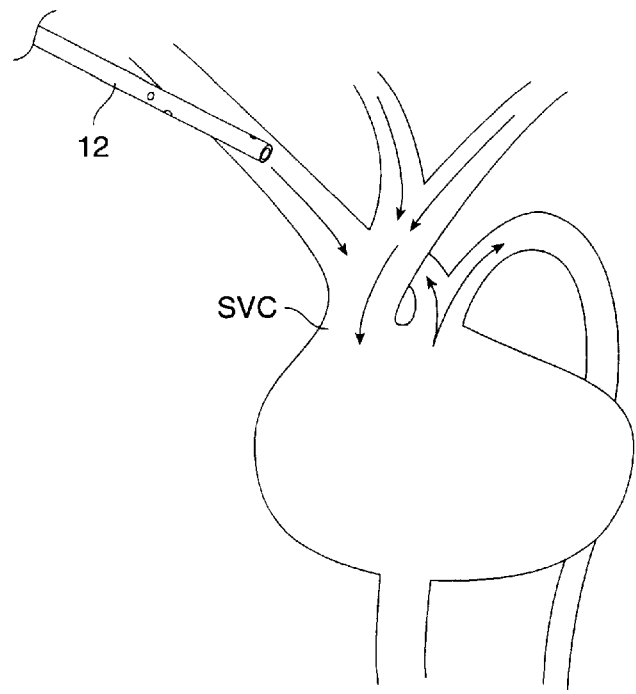
FIGS. 11A and 11B illustrate the subcutaneous implantation of the access system of FIG. 1 into a patient's jugular vein.
Figure 11B:
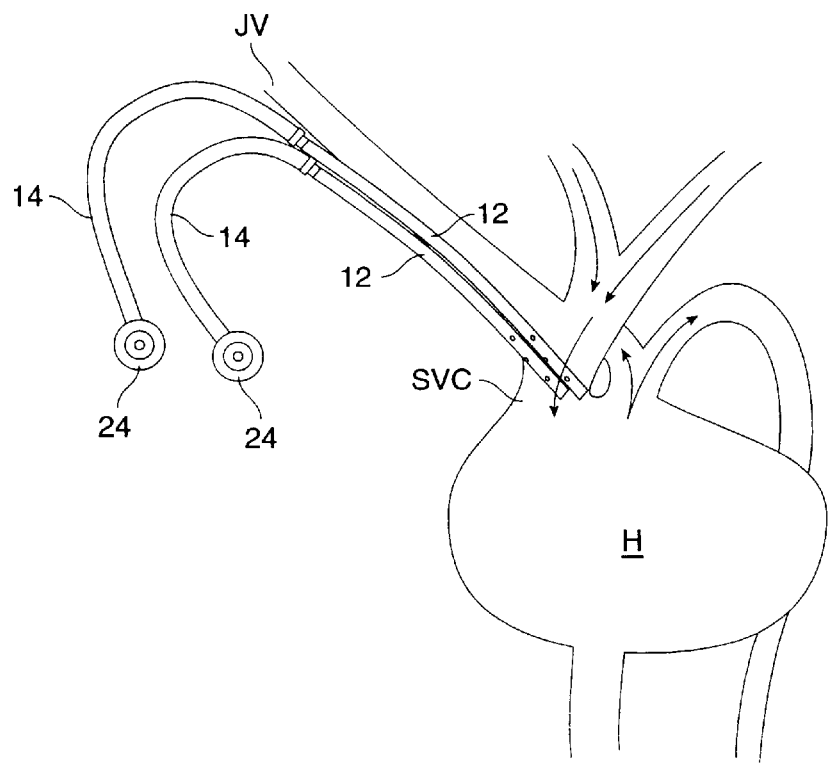

Referring in particular to FIGS. 11A and 11B, the implantation of a pair of the access cannula systems of FIG. 1 into the jugular vein JV will be described. The access cannulas 10 may be implanted by either a cut-down procedure or by the Seldinger technique. The cut-down procedure will be described first. After appropriately preparing and anesthetizing the patient, a small venotomy is performed at the desired site in the jugular vein JV, typically from 5 cm to 10 cm above the junction of the superior vena cava SVC and the right atrium of the heart. The distal tip of a first distal access cannula 12 is then inserted through the incision in the vascular wall, as illustrated in FIG. 11A, until it reaches the junction of the superior vena cava SVC and the right atrium. A second distal access cannula 12 will be inserted through the same incision so that its distal tip is located approximately 4 cm above the distal tip of the first cannula, as shown in FIG. 11B. The positioning of the distal tips of the distal access cannulas 12 is verified by X-ray.

When using the Seldinger technique, an introducer needle is penetrated through the wall of the vein at the desired insertion site. After aspirating to assure proper placement, the syringe is removed from the needle, and a guidewire inserted through the needle into the vein. The needle is then withdrawn over the guidewire, and the cutaneous puncture site enlarged with a scalpel. A second introducer needle and guidewire are then introduced through the wall of the vein at a site approximately 3 mm away from the first. A sheath/dilator is then introduced over each guidewire into the venous lumen, and one of the dilators and guidewires removed from one of the sheaths. After irrigating the distal access cannulas with heparinized saline, the distal tip is introduced through the available sheath and into the venous lumen until the tip is positioned at the junction of the superior vena cava SVC and the right atrium. The second distal access cannula 12 is introduced through the second sheath in the same fashion. The tips of the two distal access cannulas 12 are adjusted so that they lie approximately 4 cm apart, and the position confirmed with X-ray.

The placement site for each of the implantable ports 24 is selected based on a number of criteria. The infraclavicular fossa is generally satisfactory, but the actual site may vary depending on the patient characteristics. The implantable port 24 should be located in an anatomic area that provides for good stability, does not interfere with patient mobility, create pressure points, or interfere with clothing. Placement should allow for a proper amount of overlying cutaneous tissue, with an optimum tissue thickness in the range from 5 mm to 15 mm. Sufficient space should be available for placement of two implantable catheters when blood circulation through a single venous location is to be effected.

After the port implantation site is selected, a subcutaneous pocket is formed by a cut-down procedure using blunt dissection. The pocket should be sufficiently large to accommodate the port 24 and allow positioning of the port away from the incision. After the pocket is created, a tunnel is created between the pocket and the venous entry site using a tunneling tool. The distal end 18 of the proximal access cannula 12 is then trimmed so that it terminates at the venous entry site with sufficient slack for body movement and subcutaneous connection. The trimmed distal end of the proximal access cannula is then placed over the larger attachment aperture 34 on the connector 16, and secured with a suture or other biocompatible filament within the reduced diameter region 42. After trimming the proximal end 20 of the distal access cannula 12 to the proper length, the smaller attachment aperture 32 of the connector 16 is then inserted into the trimmed end. The connector 16 is then secured to the distal access cannula using a suture or other biocompatible filament placed over the region 40. The corresponding port 24 should then be finally positioned within the subcutaneous pocket, and the base secured to the underlying facia using a non-absorbable monofilament suture. The incisions can then be cleaned and closed after verifying the proper positioning and connection of all system components. The final placement is illustrated in FIG. 11B.

Figure 12:
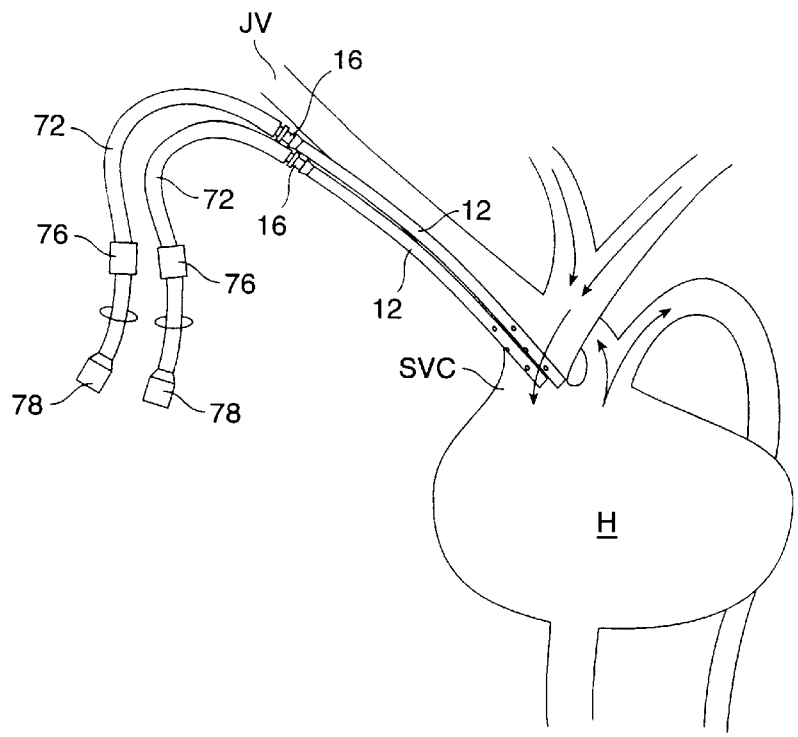
FIG. 12 illustrates the transcutaneous placement of the access system of FIG. 5 into a patient's jugular vein.

The transcutaneous catheter systems 70 can be implanted in the jugular vein JV in an analogous manner, as illustrated in FIG. 12. Implantation of the distal access cannulas 12 can be identical. The transcutaneous proximal access cannulas 72 are transcutaneously positioned and advanced to the venous access site in a manner analogous to placement of conventional transcutaneous catheters, except for the fact that they are connected to the connectors 16 after trimming, as generally described above.

Figure 13:
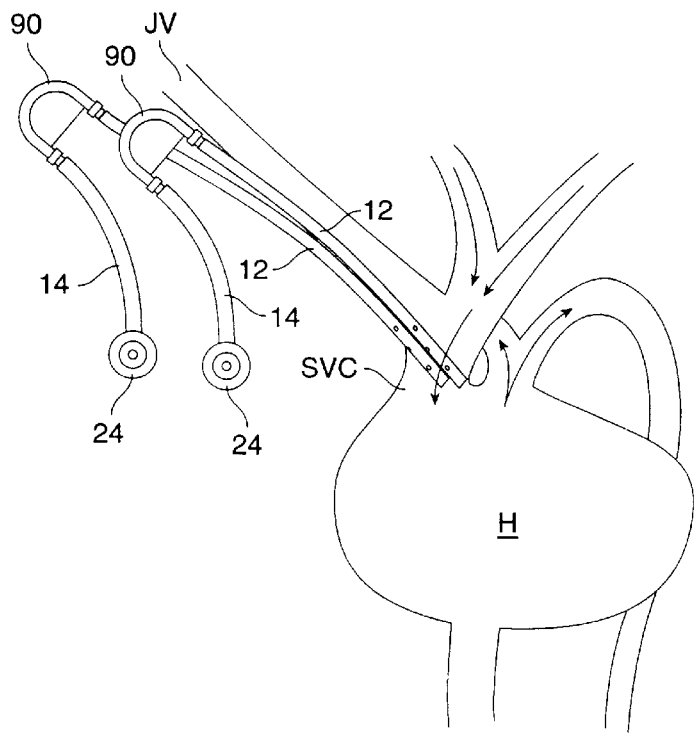
FIG. 13 illustrates the use of the connector of FIG. 6 for implanting the access system of FIG. 1 into a patient's jugular vein.

The use of remote connectors 90 for connecting the distal access cannulas 12 and proximal access cannulas 14 of the system of FIG. 1 is illustrated in FIG. 13. The connectors 90 facilitate the reversal in direction between the distal access cannulas 12 and proximal access cannulas 14. As shown in FIG. 13, the connectors 90 are located at a site remote from both the venous access site and location of the implantable ports 24. This will generally require either a larger incision or a third incision. It will be possible to locate the connectors 90 closer to the venous penetration site in many instances in order to reduce the size and/or number of penetrations required.

Figure 14:
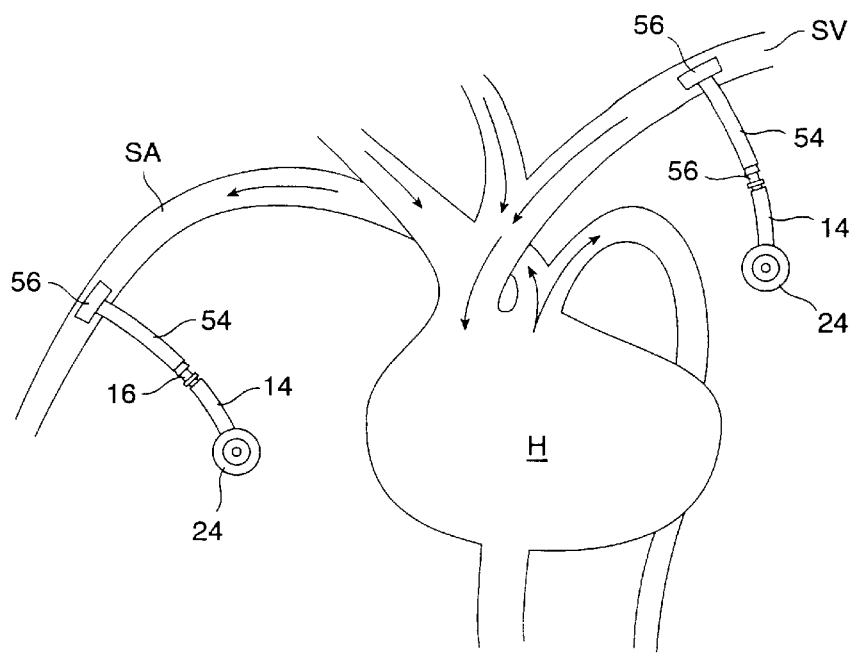
FIG. 14 illustrates the implantation of the access system of FIG. 3 into a patient's artery and vein.

Placement of the cannula access systems 50 of FIG. 3 at separate venous and arterial sites is illustrated in FIG. 14. A cross-tube connector 56 of a first distal access cannula 54 may be positioned in the subclavian artery SA, as illustrated with the connector 16 and proximal access cannula 14 located on the patient's right side. A second cross-tube 56 may be introduced into a subclavian vein SV with the connector 16, proximal access cannula 14, and implantable port 24 located on the patient's left side. Circulation between the subclavian artery SA and subclavian vein SV may then be established by percutaneous connection to the implantable ports 24.

Figure 15A:
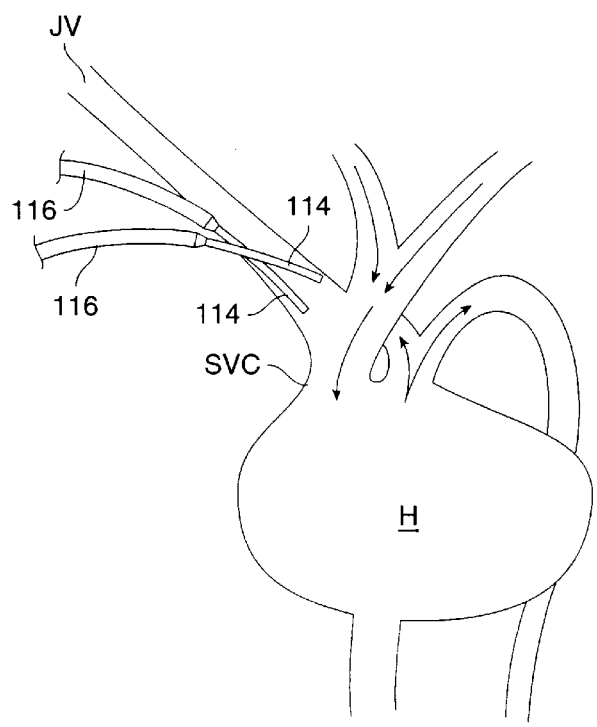
FIGS. 15A and 15B illustrate implantation of the access cannula of FIG. 9 into a patient's jugular vein.
Figure 15B:
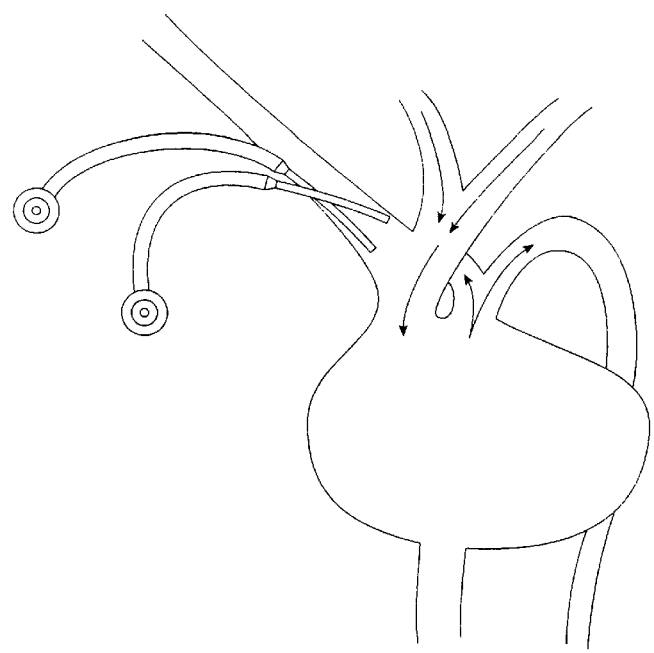

Implantation of single tube access cannulas 110 of FIG. 9 is illustrated in FIGS. 15A and 15B. The distal portions of the cannulas 114 may be introduced into the jugular vein JV in a manner analogous to those described in connection with FIGS. 11A and 11B. After location of the implantable ports 24, as illustrated in FIG. 15B, passage can be tunneled between the vein and the port location. The proximal portions 116 of the cannula 110 may then be subcutaneously positioned between the vein and the port locations, cut to length, and connected to the ports.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for establishing access to a body lumen in a patient, said method comprising:
    implanting a distal access cannula between the body lumen and a subcutaneous junction location;
    implanting a proximal access cannula between the subcutaneous junction location and a catheter connection location;
    adjusting the length of at least one of the distal access cannula and the proximal access cannula; and
    connecting a proximal end of the distal access cannula to a distal end of the proximal access cannula at the subcutaneous junction location.

2. A method as in claim 1, wherein the adjusting step comprises adjusting the length of both the distal access cannula and the proximal access.

3. A method as in claim 1, wherein the adjusting step comprises cutting the end of the distal access cannula adjacent to the subcutaneous junction location.

4. A method as in claim 3, wherein the distal access cannula is cut after the distal access cannula has been implanted.

5. A method as in claim 3, wherein the distal access cannula is cut prior to the implanting step.

6. A method as in claim 1, wherein the subcutaneous junction location is immediately adjacent to the body lumen.

7. A method as in claim 6, wherein the subcutaneous junction location is from 0 cm to 5 cm from the body lumen.

8. A method as in claim 1, wherein the subcutaneous junction location is from 5 cm to 50 cm from the body lumen.

9. A method as in claim 1, wherein the distal access cannula implanting step comprises introducing a distal end of said cannula through a body membrane into the body lumen.

10. A method as in claim 9, wherein the body lumen is a blood vessel and the distal end of the distal access cannula is connected through an incision or needle-penetration in the blood vessel wall.

11. A method as in claim 10, wherein the distal end of the cannula comprises a cross-tube which is implanted through the incision.

12. A method as in claim 10, wherein at least 1 cm of the distal end of the cannula is implanted to lie within the blood vessel lumen in an in-dwelling manner.

13. A method as in claim 9, wherein the distal end of the cannula is connected to the blood vessel wall by an end-to-side anastomosis.

14. A method as in claim 1, wherein the proximal access cannula implanting step comprises passing a proximal end of said cannula transcutaneously to provide external access to said proximal end.

15. A method as in claim 14, wherein the proximal end of the proximal access cannula comprises a connector adapted for removable connection to an external catheter.

16. A method as in claim 1, wherein the proximal access cannula implanting step comprises subcutaneously implanting a port which is connected to a proximal end of said cannula.

17. A method as in claim 1, wherein the distal access cannula and the proximal access cannula have substantially equal lumenal diameters.

18. A method as in claim 17, wherein the lumenal diameters are in the range from 1 mm to 10 mm.

19. A method as in claim 1, wherein the distal access cannula has at least a distal lumenal diameter which is less than a lumenal diameter of the proximal access cannula.

20. A method as in claim 19, wherein distal lumenal diameter of the distal access cannula is in the range from 1 mm to 6 mm and the lumenal diameter of the proximal access cannula is in the range from 3 mm to 10 mm.

21. A method as in claim 1, wherein lumenal diameter of the distal access cannula is substantially uniform over its entire length.

22. A method as in claim 1, wherein the lumenal diameter of the distal access cannula is larger over its proximal region than over its distal region.

23. A method as in claim 1, wherein the connecting step comprises providing a connector having a first attachment aperture and a second attachment aperture and a lumen therebetween, attaching the proximal end of the distal access cannula to the first attachment aperture, and attaching the distal end of the proximal access cannula to the second attachment aperture.

24. A method as in claim 23, wherein the first and second attachment apertures are disposed at a relative angle in the range from 45° to 270°.

25. A method as in claim 24, wherein the relative angle is in the range from 90° to 180°.

26. A method as in claim 24, wherein the connector comprises an angled tube having a spanning web to inhibit tissue in-growth.

27. A method as in claim 23, wherein the first and second attachment apertures are coaxially aligned.

28. An improved method for establishing access between a body lumen having a subcutaneous penetration in a lumenal wall and an implanted port, said method being of the type wherein a cannula having a first end, a second end, and subcutaneously attached at the first end to the penetration in the lumenal wall of the body lumen and attached at the second end to the port, wherein the improvement comprises implanting a cannula wherein the cannula lumen is larger in a region at the second end connected to the port than at the first end connected to the body lumen penetration, wherein the cannula lumen diameter in the first end connected to the body lumen wall penetration is in the range from 1 mm to 6 mm and the cannula lumen diameter in the second end connected to the port is in the range from 3 mm to 10 mm.

29. A method for establishing access to a body lumen in a patient, said method comprising:
providing an access cannula having a small diameter distal region and a large diameter proximal region; and
implanting the access catheter so that the small diameter distal region is connected to the body lumen with a distal end of the large diameter proximal region located subcutaneously, wherein a proximal end of the proximal region is available for connection to a catheter, wherein the distal region lumenal diameter is in the range from 1 mm to 6 mm and the proximal lumenal diameter is in the range 3 mm to 10 mm.

30. A method as in claim 29, wherein lumenal diameter of the distal region of the access cannula is substantially uniform over its entire length.

31. A method as in claim 30, wherein the lumenal diameter of the proximal region of the access cannula is substantially uniform over its entire length.

32. A method as in claim 29, wherein the access cannula implanting step comprises introducing a distal end of said cannula through a body membrane into the body lumen.

33. A method as in claim 32, wherein the body lumen is a blood vessel and the distal end of the distal access cannula is connected to an incision or needle-penetration in the blood vessel wall.

34. A method as in claim 33, wherein the distal end of the cannula comprises a cross-tube which is implanted through the incision.

35. A method as in claim 33, wherein at least 1 cm of the distal end of the cannula is implanted to lie within the blood vessel lumen in an in-dwelling manner.

36. A method as in claim 29, wherein the distal end of the access cannula is connected to the blood vessel wall by an end-to-side anastomosis.

37. A method as in claim 29, wherein the access cannula implanting step comprises passing a proximal end of said cannula transcutaneously to provide external access to said proximal end.

38. A method as in claim 37, wherein the proximal end of the proximal access cannula comprises a connector adapted for removable connection to the an external catheter.

39. A method as in claim 29, wherein the access cannula implanting step comprises subcutaneously implanting a port which is connected to a proximal end of said cannula.

40. A method as in claim 29, wherein the access cannula comprises a distal portion and a proximal portion and wherein the implanting step comprises connecting a proximal end of the distal portion to a distal end of the proximal portion at a subcutaneous junction location.

41. A method as in claim 40, wherein the distal portion and the distal region are coextensive and wherein the proximal portion and the proximal region are coextensive.

42. A method as in claim 40, wherein the distal portion comprises both the distal region and a port of the proximal region.

43. A method as in claim 40, wherein the subcutaneous junction location is immediately adjacent to the body lumen.

44. A method as in claim 43, wherein the subcutaneous junction location is from 0 cm to 5 cm from the body lumen.

45. A method as in claim 40, wherein the subcutaneous junction location is from 5 cm to 50 cm from the body lumen.

46. A method as in claim 40, wherein the connecting step comprises providing a connector having a first attachment aperture and a second attachment aperture and a lumen therebetween, attaching the proximal end of the distal portion of the access cannula to the first attachment aperture, and attaching the distal end of the proximal portion of the access cannula to the second attachment aperture.

47. A method as in claim 46, wherein the first and second attachment apertures are disposed at a relative angle in the range from 45° to 270°.

48. A method as in claim 47, wherein the relative angle is in the range from 90° to 180°.

49. A method as in claim 47, wherein the connector comprises an angled tube having spanning a web to inhibit tissue in-growth.

50. A method as in claim 46, wherein the first and second attachment apertures are coaxially aligned.

51. A method as in claim 40, further comprising adjusting the length of at least one of the distal portion and the proximal portion of the access catheter prior to the connecting step.

52. A method as in claim 51, wherein the adjusting step comprises adjusting the length of both the distal access cannula and the proximal access cannula.

53. A method as in claim 52, wherein the adjusting step comprises cutting the end of the cannula adjacent to the subcutaneous junction location.

54. A method as in claim 53, wherein the cannula is cut after the cannula has been implanted.

55. A method as in claim 53, wherein the cannula is cut prior to the implanting step.

56. A method for establishing access to a body lumen in a patient, said method comprising:
providing an access cannula having a small diameter distal region and a large diameter proximal region; and
implanting the access catheter so that the small diameter distal region is connected through a wall of the body lumen which comprises a blood vessel lumen with a distal end of the large diameter proximal region located subcutaneously, wherein a proximal end of the proximal region is available for connection to a catheter, wherein at least 1 cm of the distal end of the cannula is implanted to lie within the blood vessel lumen in an in-dwelling manner.

57. A method as in claim 56, wherein distal region lumenal diameter is in the range from 1 mm to 6 mm and the proximal lumenal diameter is in the range 3 mm to 10 mm.

58. A method as in claim 57, wherein lumenal diameter of the distal region of the access cannula is substantially uniform over its entire length.

59. A method as in claim 58, wherein the lumenal diameter of the proximal region of the access cannula is substantially uniform over its entire length.

60. A method as in claim 56, wherein the access cannula implanting step comprises introducing a distal end of said cannula through a blood vessel wall into the blood vessel lumen.

61. A method as in claim 60, wherein the distal end of the distal access cannula is connected to an incision or needle-penetration in the blood vessel wall.

62. A method as in claim 61, wherein the distal end of the cannula comprises a cross-tube which is implanted through the incision.

63. A method as in claim 56, wherein the distal end of the access cannula is connected to the blood vessel wall by an end-to-side anastomosis.

64. A method as in claim 56, wherein the access cannula implanting step comprises passing a proximal end of said cannula transcutaneously to provide external access to said proximal end.

65. A method as in claim 64, wherein the proximal end of the proximal access cannula comprises a connector adapted for removable connection to the an external catheter.

66. A method as in claim 56, wherein the access cannula implanting step comprises subcutaneously implanting a port which is connected to a proximal end of said cannula.

67. A method as in claim 56, wherein the access cannula comprises a distal portion and a proximal portion and wherein the implanting step comprises connecting a proximal end of the distal portion to a distal end of the proximal portion at a subcutaneous junction location.

68. A method as in claim 67, wherein the distal portion and the distal region are coextensive and wherein the proximal portion and the proximal region are coextensive.

69. A method as in claim 67, wherein the distal portion comprises both the distal region and a port of the proximal region.

70. A method as in claim 67, wherein the subcutaneous junction location is immediately adjacent to the body lumen.

71. A method as in claim 70, wherein the subcutaneous junction location is from 0 cm to 5 cm from the body lumen.

72. A method as in claim 67, wherein the subcutaneous junction location is from 5 cm to 50 cm from the body lumen.

73. A method as in claim 67, wherein the connecting step comprises providing a connector having a first attachment aperture and a second attachment aperture and a lumen therebetween, attaching the proximal end of the distal portion of the access cannula to the first attachment aperture, and attaching the distal end of the proximal portion of the access cannula to the second attachment aperture.

74. A method as in claim 73, wherein the first and second attachment apertures are disposed at a relative angle in the range from 45° to 270°.

75. A method as in claim 74, wherein the relative angle is in the range from 90° to 180°.

76. A method as in claim 74, wherein the connector comprises an angled tube having a spanning web to inhibit tissue in-growth.

77. A method as in claim 73, wherein the first and second attachment apertures are coaxially aligned.

78. A method as in claim 58, further comprising adjusting the length of at least one of the distal portion and the proximal portion of the access catheter prior to the connecting step.

79. A method as in claim 78, wherein the adjusting step comprises adjusting the length of both the distal access cannula and the proximal access cannula.

80. A method as in claim 79, wherein the adjusting step comprises cutting the end of the cannula adjacent to the subcutaneous junction location.

81. A method as in claim 80, wherein the cannula is cut after the cannula has been implanted.

82. A method as in claim 80, wherein the cannula is cut prior to the implanting step.

83. A method for establishing access to a body lumen in a patient, said method comprising:
providing an access cannula having a small diameter distal region and a large diameter proximal region; and
implanting the access catheter so that the small diameter distal region is connected to the body lumen with a distal end of the large diameter proximal region located subcutaneously, wherein a proximal end of the proximal region is available for connection to a catheter, wherein the distal end of the access cannula is connected to a blood vessel wall by an end-to-side anastomosis.

84. A method as in claim 83, wherein distal region lumenal diameter is in the range from 1 mm to 6 mm and the proximal lumenal diameter is in the range 3 mm to 10 mm.

85. A method as in claim 84, wherein lumenal diameter of the distal region of the access cannula is substantially uniform over its entire length.

86. A method as in claim 85, wherein the lumenal diameter of the proximal region of the access cannula is substantially uniform over its entire length.

87. A method as in claim 83, wherein the access cannula implanting step comprises passing a proximal end of said cannula transcutaneously to provide external access to said proximal end.

88. A method as in claim 87, wherein the proximal end of the proximal access cannula comprises a connector adapted for removable connection to the an external catheter.

89. A method as in claim 83, wherein the access cannula implanting step comprises subcutaneously implanting a port which is connected to a proximal end of said cannula.

90. A method as in claim 83, wherein the access cannula comprises a distal portion and a proximal portion and wherein the implanting step comprises connecting a proximal end of the distal portion to a distal end of the proximal portion at a subcutaneous junction location.

91. A method as in claim 90, wherein the distal portion and the distal region are coextensive and wherein the proximal portion and the proximal region are coextensive.

92. A method as in claim 90, wherein the distal portion comprises both the distal region and a port of the proximal region.

93. A method as in claim 93, wherein the subcutaneous junction location is immediately adjacent to the body lumen.

94. A method as in claim 90, wherein the subcutaneous junction location is from 0 cm to 5 cm from the body lumen.

95. A method as in claim 90, wherein the subcutaneous junction location is from 5 cm to 50 cm from the body lumen.

96. A method as in claim 90, wherein the connecting step comprises providing a connector having a first attachment aperture and a second attachment aperture and a lumen therebetween, attaching the proximal end of the distal portion of the access cannula to the first attachment aperture, and attaching the distal end of the proximal portion of the access cannula to the second attachment aperture.

97. A method as in claim 96, wherein the first and second attachment apertures are disposed at a relative angle in the range from 45° to 270°.

98. A method as in claim 97, wherein the relative angle is in the range from 90° to 180°.

99. A method as in claim 97, wherein the connector comprises an angled tube having a spanning web to inhibit tissue in-growth.

100. A method as in claim 96, wherein the first and second attachment apertures are coaxially aligned.

101. A method as in claim 90, further comprising adjusting the length of at least one of the distal portion and the proximal portion of the access catheter prior to the connecting step.

102. A method as in claim 101, wherein the adjusting step comprises adjusting the length of both the distal access cannula and the proximal access cannula.

103. A method as in claim 102, wherein the adjusting step comprises cutting the end of the cannula adjacent to the subcutaneous junction location.

104. A method as in claim 103, wherein the cannula is cut after the cannula has been implanted.

105. A method as in claim 103, wherein the cannula is cut prior to the implanting step.

106. A method for establishing access to a body lumen in a patient, said method comprising:
providing an access cannula having a small diameter distal region and a large diameter proximal region; and
implanting the access catheter so that the small diameter distal region is connected to the body lumen with a distal end of the large diameter proximal region located subcutaneously, wherein a proximal end of the proximal region is available for connection to a catheter, wherein the access cannula implanting step comprises passing a proximal end of said cannula transcutaneously to provide external access to said proximal end.

107. A method as in claim 106, wherein distal region lumenal diameter is in the range from 1 mm to 6 mm and the proximal lumenal diameter is in the range 3 mm to 10 mm.

108. A method as in claim 107, wherein lumenal diameter of the distal region of the access cannula is substantially uniform over its entire length.

109. A method as in claim 108, wherein the lumenal diameter of the proximal region of the access cannula is substantially uniform over its entire length.

110. A method as in claim 106, wherein the access cannula implanting step comprises introducing a distal end of said cannula through a body membrane into the body lumen.

111. A method as in claim 110, wherein the body lumen is a blood vessel and the distal end of the distal access cannula is connected to an incision or needle-penetration in the blood vessel wall.

112. A method as in claim 111, wherein the distal end of the cannula comprises a cross-tube which is implanted through the incision.

113. A method as in claim 111, wherein at least 1 cm of the distal end of the cannula is implanted to be within the blood vessel lumen in an in-dwelling manner.

114. A method as in claim 106, wherein the distal end of the access cannula is connected to the blood vessel wall by an end-to-side anastomosis.

115. A method as in claim 106, wherein the proximal end of the proximal access cannula comprises a connector adapted for removable connection to the an external catheter.

116. A method as in claim 106, wherein the access cannula comprises a distal portion and a proximal portion and wherein the implanting step comprises connecting a proximal end of the distal portion to a distal end of the proximal portion at a subcutaneous junction location.

117. A method as in claim 116, wherein the distal portion and the distal region are coextensive and wherein the proximal portion and the proximal region are coextensive.

118. A method as in claim 116, wherein the distal portion comprises both the distal region and a port of the proximal region.

119. A method as in claim 116, wherein the subcutaneous junction location is immediately adjacent to the body lumen.

120. A method as in claim 119, wherein the subcutaneous junction location is from 0 cm to 5 cm from the body lumen.

121. A method as in claim 116, wherein the subcutaneous junction location is from 5 cm to 50 cm from the body lumen.

122. A method as in claim 116, wherein the connecting step comprises providing a connector having a first attachment aperture and a second attachment aperture and a lumen therebetween, attaching the proximal end of the distal portion of the access cannula to the first attachment aperture, and attaching the distal end of the proximal portion of the access cannula to the second attachment aperture.

123. A method as in claim 122, wherein the first and second attachment apertures are disposed at a relative angle in the range from 45° to 270°.

124. A method as in claim 123, wherein the relative angle is in the range from 90° to 180°.

125. A method as in claim 123, wherein the connector comprises an angled tube having a spanning web to inhibit tissue in-growth.

126. A method as in claim 122, wherein the first and second attachment apertures are coaxially aligned.

127. A method as in claim 116, further comprising adjusting the length of at least one of the distal portion and the proximal portion of the access catheter prior to the connecting step.

128. A method as in claim 127, wherein the adjusting step comprises adjusting the length of both the distal access cannula and the proximal access cannula.

129. A method as in claim 128, wherein the adjusting step comprises cutting the end of the cannula adjacent to the subcutaneous junction location.

130. A method as in claim 129, wherein the cannula is cut after the cannula has been implanted.

131. A method as in claim 129, wherein the cannula is cut prior to the implanting step.

* * * * *

UNITED STATES PATENT AND TRADEMARK OFFICE
CERTIFICATE OF CORRECTION

PATENT NO. : 5,931,829

DATED : August 3, 1999

INVENTOR(S) : Burbank, et al

It is certified that error appears in the above-identified patent and that said Letters Patent is hereby corrected as shown below:

On the Title Page, Item [75] should read:

[75] Inventors: Jeffrey H. Burbank, Boxford, Mass.; James M. Brugger, Newburyport, Mass.; Charles D. Finch, Clinton, Miss.; Gerald Beathard, Austin, Tex.; George W. Buffaloe, Arvada, Colo., all of United States of America.

Signed and Sealed this

Third Day of April, 2001

Attest:

NICHOLAS P. GODICI

Attesting Officer

Acting Director of the United States Patent and Trademark Office